(12) United States Patent
Ferrari

(10) Patent No.: US 6,184,988 B1
(45) Date of Patent: Feb. 6, 2001

(54) AUTOMATIC DEVICE FOR DETERMINING PRINT QUALITY ON BOTTLES OF ANY SHAPE

(75) Inventor: Vittorio Ferrari, Reggio Emilia (IT)

(73) Assignee: O.M.S.O. S.p.A., Via Adige (IT)

( * ) Notice: Under 35 U.S.C. 154(b), the term of this patent shall be extended for 0 days.

(21) Appl. No.: 09/407,886

(22) Filed: Sep. 29, 1999

(30) Foreign Application Priority Data

Oct. 22, 1998 (IT) ............................................. RE98A0104

(51) Int. Cl.$^7$ ................................................. G01N 21/90
(52) U.S. Cl. ....................................... 356/428; 356/240.1
(58) Field of Search ............................... 356/239.1, 239.3, 356/239.4, 239.7, 239.8, 240.1, 428, 402, 404, 425

(56) References Cited

FOREIGN PATENT DOCUMENTS

| 0516968 | 12/1992 | (EP) . |
| 0802054 | 10/1997 | (EP) . |

*Primary Examiner*—Frank G. Font
*Assistant Examiner*—Roy M. Punnoose

(74) *Attorney, Agent, or Firm*—Birch, Stewart, Kolasch & Birch, LLP

(57) ABSTRACT

An automatic device for determining print quality on bottles of circular, elliptical or polygonal cross-section, comprising at least one print quality inspection station in which a cylindrical portion of the image surface is photographed by a camera or video camera, means for transferring the object to successive inspection stations in succession, in each of which a further portion of the image is photographed, means for assembling the images acquired in each inspection station to obtain the overall image of all the photographed portions, comparator means for comparing the overall image with a reference image, and means for indicating non-conformity between the overall acquired image and the reference image and for operating an actuator which feeds the object carrying the non-conforming overall image to a rejected object collection line, in which a single inspection station comprises means for rotating the image-carrying object through an angle of at least 360° with continuity, one video camera arranged to photograph in succession an image portion after each rotation of the bottle through an angle equal to 360° divided by the total number of images to be acquired, means for assembling the acquired images to obtain the overall image of all the portions photographed, and comparator means for comparing the overall image with a reference image.

13 Claims, 5 Drawing Sheets

AUTOMATIC DEVICE FOR DETERMINING PRINT QUALITY ON BOTTLES OF ANY SHAPE

BACKGROUND OF THE INVENTION

The present invention relates to devices for monitoring the quality of silk-screen printing on plastic or glass bottles of any shape.

In the known art this monitoring is effected by video cameras arranged to photograph individual images of the object to be inspected in successive positions, and compare them with a like number of reference images to determine any discrepancies.

In particular, the known devices for monitoring print quality on bottles of circular cross-section comprise a number of successive inspection stations, in each of which a video camera photographs the image of the bottle to be inspected in a determined position.

If the device comprises two stations the bottle is rotated through 180° prior to the second station, so that by placing the two acquired images side by side an image of the entire bottle surface is reconstructed, this then being compared with the reference image.

If there are three image inspection stations, the bottle has to be rotated through 120° prior to each station following the first.

It is also known that the photographic image of a circular or otherwise non-flat object presents distortions commencing from the centre plane. These distortions are greater the smaller the radius of curvature of the object surface, and the larger the lens opening angle, for equal distances between the object centre and the lens. Consequently the known devices have the drawback of lack of photographic accuracy in proximity to the lateral portions of the image.

In the known art this drawback is reduced by providing at least four inspection stations each comprising its own video camera, and means for rotating the object through 90° between one station and the next, but this in addition to being complicated is also of high cost.

SUMMARY OF THE INVENTION

The object of the present invention is to overcome the stated drawbacks within the framework of a flexible, rational and low-cost solution.

This object is attained according to the invention by a device for determining the quality of silk-screen printing on objects which comprises only one image inspection station provided with a single video camera and, upstream of the inspection station, an initial positioning station for the bottle to be inspected.

Specifically, the invention uses a single video camera arranged to acquire at least two successive images of the bottle while this is rotated at constant speed by suitable means within the single inspection station.

Said images are acquired by known means, each image being acquired after each rotation of the bottle through an angle equal to 360° divided by the total number of images to be acquired.

The invention also comprises upstream of the inspection station a positioning station in which the bottle is positioned with the desired orientation relative to a fixed angular reference device. This is achieved by suitable means for sensing a fixed reference device positioned on the bottle and arranged to interact with it to position the bottle with the required orientation.

The acquired images are then compared with a reference image to evaluate any print imperfections. The invention is also provided with selector means arranged to separate those bottles presenting imperfections from those judged perfect during inspection.

BRIEF DESCRIPTION OF THE DRAWINGS

The constructional characteristics of the invention will be more apparent from the ensuing description of a preferred embodiment thereof illustrated in the accompanying drawings, wherein.

DETAILED DESCRIPTION OF THE INVENTION

Figure 3:
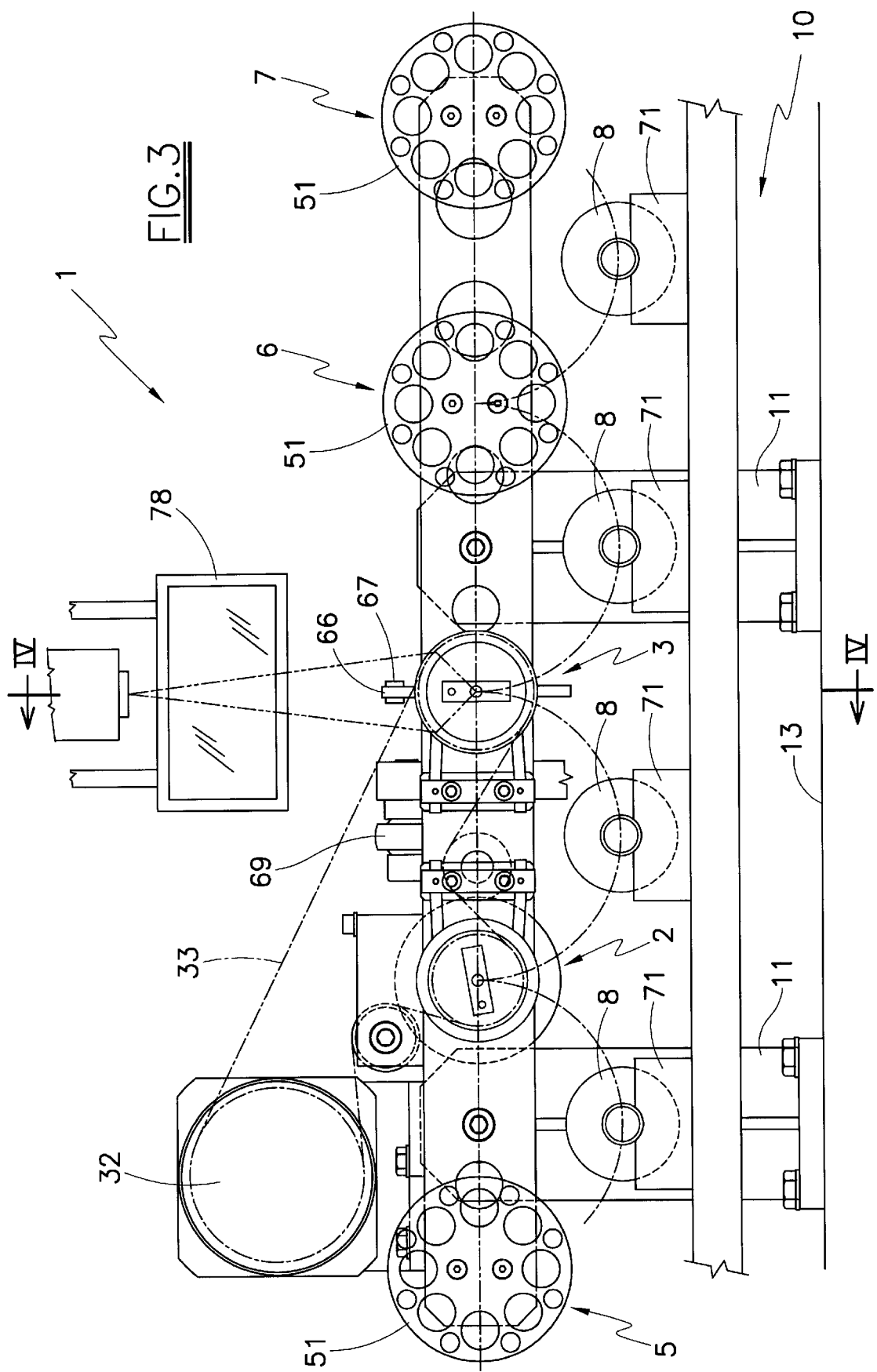
FIG. 3 is a section taken along line III—III of FIG. 2.
Figure 4:
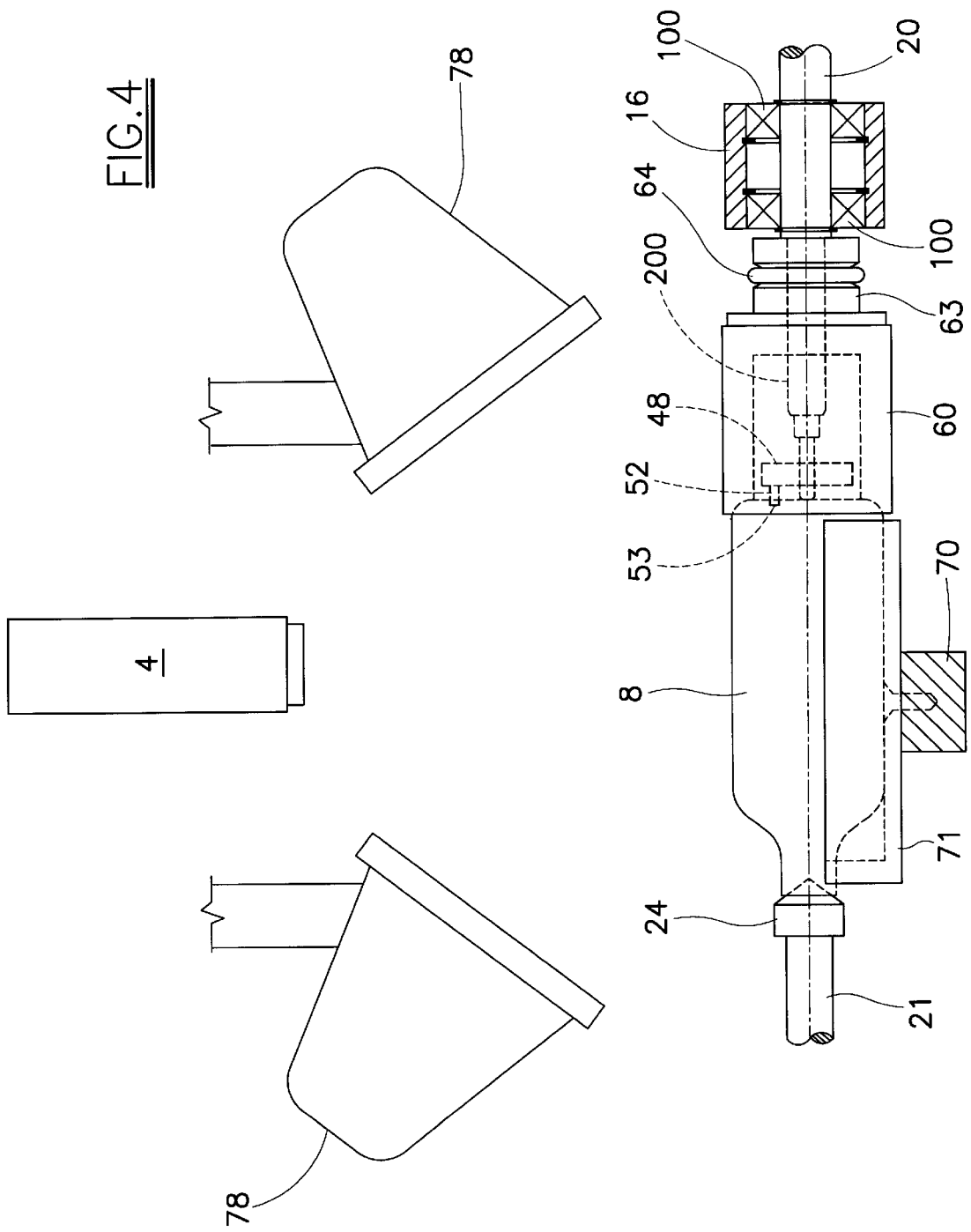
FIG. 4 is a cross-section taken along the line IV—IV of FIG. 2.

The above-described figures show the device 1 for determining the quality of silk-screen printing on bottles of circular cross-section, the device comprising a positioning station 2 preceding the image inspection and acquisition station 3. Above the station 3 and exactly coaxial with its centre, there is positioned a video camera 4 as shown in FIGS. 3 and 4.

The positioning station 2 and inspection station 3 are respectively preceded and followed by identical stations 5, 6 and 7, through which the bottle passes.

The sole purpose of the station 5 is to act as a parking station before the bottles 8 are fed to the positioning station 2, whereas the stations 6 and 7 act as intermediate stations before the bottle is fed to the selector device 9. The number of said stations 5, 6 and 7 can vary depending on the line in which the device 1 of the invention is to be installed, and in fact could be dispensed with in certain embodiments of the invention.

The device 1 for determining print quality comprises a frame 10 supporting all the stations 5, 2, 3, 6, 7, these being equidistant and aligned horizontally. Said frame 10 comprises two uprights 11 fixed to the base 13 and each supporting an internally hollow cylindrical sleeve 14 for receiving a rod 15.

Figure 1:
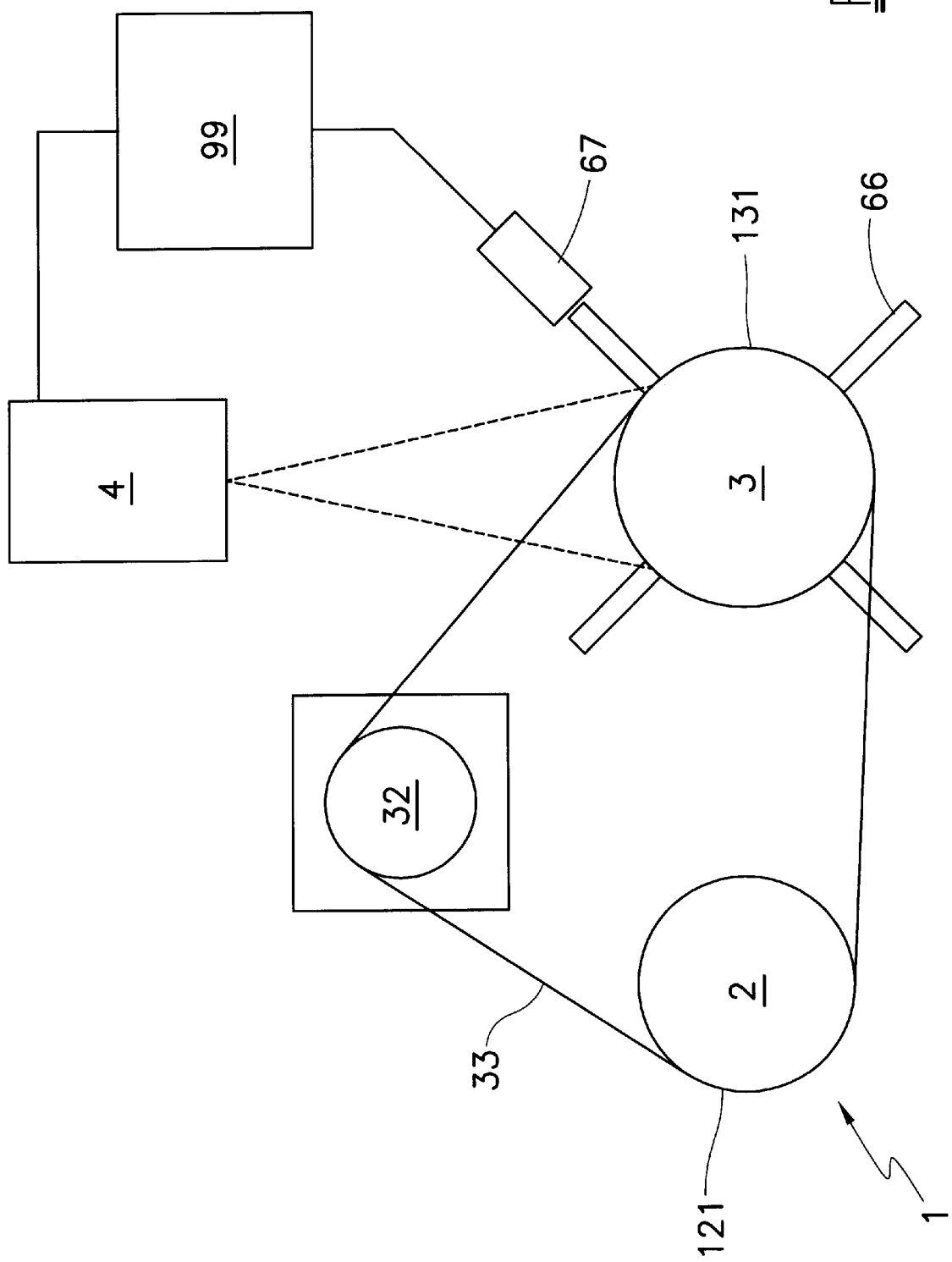
FIG. 1 is a schematic view of the device of the present invention.
Figure 2:
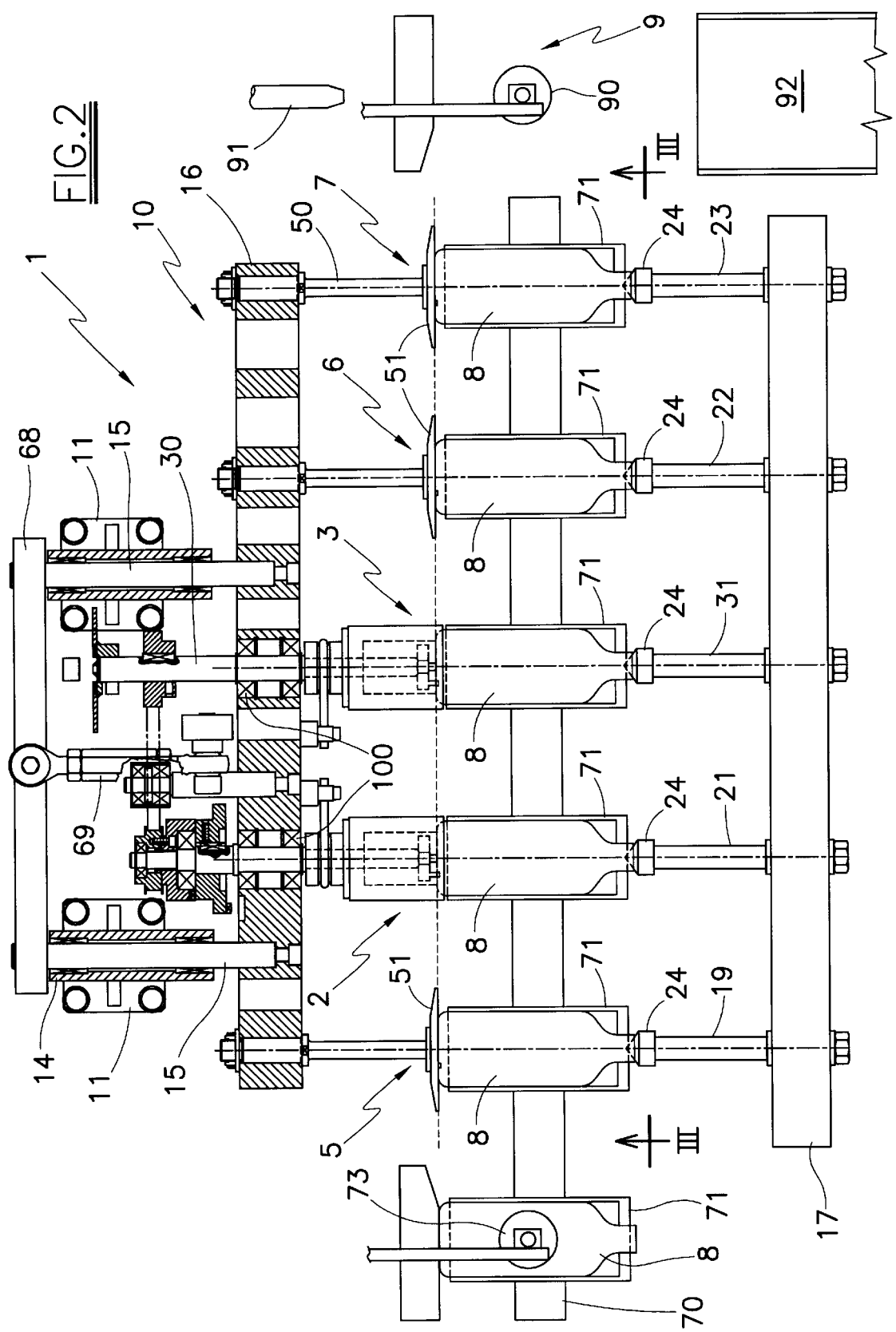
FIG. 2 is a partly sectional plan view of the device of the present invention.
Figure 5:
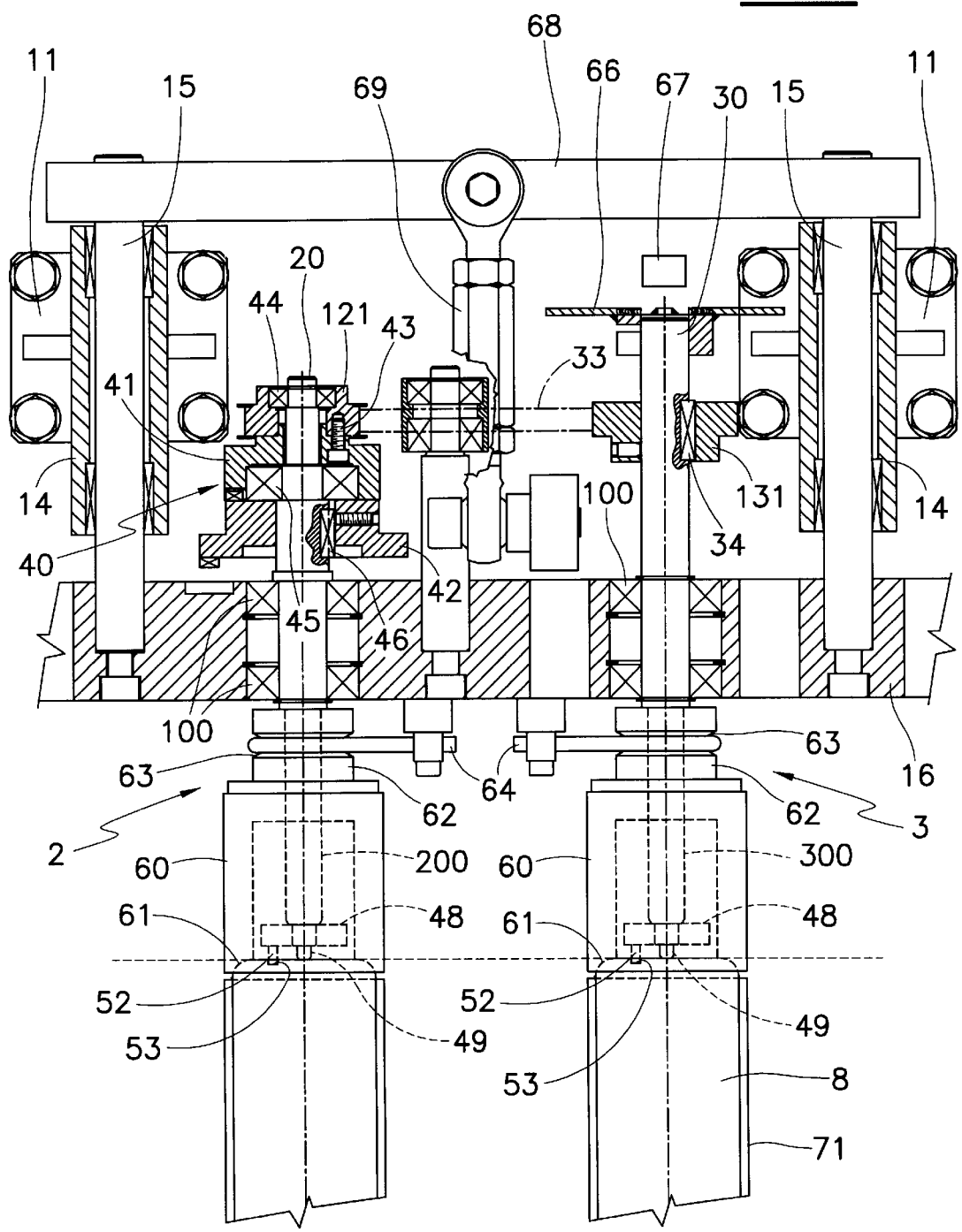
FIG. 5 is an enlargement of a part of the invention shown in FIG. 2.

With reference to FIGS. 2 and 5, to the front ends of the two rods 15 there is fixed a bar 16 having a plurality of holes for receiving shafts 50 of the stations 5, 6 and 7, and shafts 20 and 30 of the stations 2 and 3.

In front of the bar 16 there is provided a second bar 17 supporting rods 19, 20, 21, 22 and 23, all identical, which at that end facing said bar 16 comprise idly mounted frusto-conical nosepieces 24 arranged to interact with the mouth of the bottle. The rods 19, 22 and 23 are exactly coaxial with the shafts 50 of the stations 5, 6 and 7, whereas the rods 21 and 31 are coaxial with the shafts 20 and 30. At their free end, the shafts 50 support circular seats 51 arranged to interact with the base of the bottle 8.

Both the shafts 20 and 30 are mounted on the bar 16 by way of usual ball bearings 100, and are rotated by a usual pneumatic actuator 32, which transmits motion to them via a toothed belt 33 engaging two pulleys, 121 and 131 respectively, mounted on said shafts 20 and 30. The pulley 131 is coupled to the shaft 30 by a usual key 34, whereas the pulley 121 does not transmit motion directly to the shaft 20 but is coupled to a frontal clutch device 40 . Said device comprises a coupling 41 arranged to engage a flange 42.

The coupling 41 is fixed to the pulley 21 by a screw 43, the entire unit being mounted on the shaft 20 by way of ball bearings 44 and 45. The flange 42 is coupled to the shaft 20 by a key 46. Said flange 42 can slide longitudinally on the shaft 20 to be positioned in a first position in which it engages the coupling 41 to rotate the shaft 20, and in a second position in which it is disengaged from said coupling 41 but engages the bar 16. The engagement or disengagement of the flange 42 by the coupling 41 is effected by the operator on the basis of the cross-sectional shape of the bottle to be inspected, as explained hereinafter.

With reference to FIG. 5, the front part 200 and 300 of the shafts 20 and 30 which emerges from the bar 16 comprises a block 48, which is fixed to the end of said shafts and has a central hole for passage of a usual spring-loaded expeller 49 emerging from the ends of said shafts 20 and 30. In an off-centre position said block comprises a retractable pin 52 to be inserted into a reference notch 53 present in the bottle, in order to rotate this latter.

It should be noted that said front parts 200 and 300 can be formed separately from the shafts 20 and 30 and be subsequently screwed into them.

An internally hollow cup-shaped member 60 provided with an inner shoulder 61, known as the endpiece, for receiving the bottle base, is idly mounted on the parts 200 and 300 of the shafts 20 and 30. Said cup-shaped bodies comprise a rear shank 62 provided with a circular groove 63 for receiving a belt 64 which prevents or at least brakes any rotation of said members 60 during the rotation of the shafts 20 and 30. For this purpose the belt 64 is fixed to the bar 16 by known means.

On the rear end of the shaft 30 there is rigidly mounted a cross-shaped member 66, the mutually perpendicular arms of which act as an encountering member for the proximity sensor 67.

The rods 15 are connected together by a rear plate 68, to which there is fixed an arm 69 connected to an assembly of usual means for moving the plates 16 and 17 away from and towards each other.

The bottles 8 are fed to the stations 5, 2, 3, 6 and 7 by a usual conveyor 70 (moving stepwise), comprising trays 71 supporting the bottles 8. Between one station and the next the trays 71 travel through a circumferential arc, as shown in FIG. 3.

Finally, the device of the invention comprises within the station 3 two identical spotlights 73 orientated as shown in FIG. 5, to illuminate the image acquisition area.

The device 1 of the invention also comprises a control system 99 for controlling its operation, as now described.

Starting from the position shown in FIG. 2, the bars 16 and 17 are moved apart to release the bottles 8 onto the underlying trays 71, after which the conveyor 70 feeds the bottles to the next station by undergoing forward travel, ie by causing the trays 71 to travel through a circular arc in an anti-clockwise direction. Specifically, the last tray to the right of the conveyor 70 feeds the bottle 8 to the selector device 9, which supports it by means of the sucker 90. If the bottle is defective, the nozzle 91 blows an air jet against the base of the bottle, which in this manner is urged onto a chute 92, whereas if the bottle is free of defects it is withdrawn by usual means, not shown, and fed to the next production cycle. In contrast, the first tray 71, to the left of the conveyor 70, which receives the bottle from a usual sucker-type feed device 73, transfers it to the station 5.

When the bottles are in position in the stations 5, 2, 3, 6, 7 and 9, the plates 16 and 17 are advanced so that the bottles become supported between the nosepieces 24 and the seats 51 in the stations 5, 6 and 7, and between the nosepieces 24 and the members 60 in the stations 2 and 3.

The conveyor 70 then moves rearwards into its initial position. During this repositioning of the conveyor 70 the control system causes the pneumatic actuator 32 to rotate through 240°, so rotating the shafts 20 and 30.

In the positioning station 2 the bottle is maintained at rest between the nosepiece 24 and the cup 60, while the shaft 20 rotates through 450° to rotate the block 48 such that the retractable pin 52, while rotating, becomes inserted in the reference notch 53 present in the bottle. When this occurs the bottle is rotated by the shaft as far as its travel limit. In this manner the bottle is preset in a determined known position, so that when the bottle is fed to the next station 3 for image acquisition and recording, the pin 52, supported by the block 48 rigid with the shaft 30, becomes directly inserted into the reference notch present in the bottle base in order to rotate it, or at most has to be rotated through only a few degrees to enable it to be inserted in said reference notch 53.

Simultaneously with the rotation of the shaft 20, the shaft 30 rotates through 360° to rotate the bottle previously positioned in the station 2. During the rotation of the shaft 30, when the first of the arms of the cross-shaped member 66 passes in front of the proximity sensor 67, this latter causes the video camera 4 to acquire images. The video camera successively acquires one image each time one of the arms of the cross-shaped member 66 passes in front of the proximity sensor 67.

In this manner the video camera acquires four images corresponding to successive 90° rotations of the bottle. The acquired images are then compared with a reference image by suitable software which also causes the selector device 9 to reject those bottles presenting print imperfections.

When image acquisition is complete the conveyor 70 feeds the bottles to the next station, the pneumatic actuator 32 simultaneously being made to rotate in the reverse direction to return to its initial position, after which the cycle is repeated identically to the aforedescribed.

If the cross-section through the bottles to be inspected is ellipsoidal, rectangular or square, the positioning station 2 is no longer required as it is no longer necessary to align the bottle with a determined reference. Consequently the shaft 20 is made idle by disengaging the flange 42 from the coupling 41 of the frontal clutch device 40, so that rotation of the pulley 21 does not cause the shaft 20 to rotate.

In this case the cup-shaped members 60 must evidently have a shape which matches the shape of the bottle base, and the belt 64 which prevents rotation of the cup-shaped member 60 mounted on the shaft 30 is no longer required.

Again in this case, the trays 71 are replaced with trays of suitable shape.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An automatic device for determining print quality on objects of circular, elliptical or polygonal cross-section, having an image hereon, which comprises
   at least one print quality inspection station in which a cylindrical portion of the image is photographed by a camera or video camera,
   means for transferring the object to successive inspection stations in succession, in each of which a further portion of the image is photographed,
   means for assembling the images acquired in each inspection station to obtain the overall image of all the photographed portions,
   comparator means for comparing the overall image with a reference image, and
   means for indicating non-conformity between the overall acquired image and the reference image and for operating an actuator which feeds the object carrying the non-conforming overall image to a rejected object collection line, wherein
   one of the inspection stations comprises means for rotating the image-carrying object through an angle of at least 360° with continuity,
   a single video camera arranged to photograph, in succession, an image portion after each rotation of the object through an angle equal to 360° divided by the total number of images to be acquired,
   means for assembling the acquired images to obtain the overall image of all the portions photographed, and
   comparator means for comparing the overall image with a reference image.

2. The device as claimed in claim 1, comprising an inspection station and, upstream thereof, a positioning station, in both of which an idly mounted nosepiece and an idly mounted seat, which are suitably braked, support the object and are caused to rotate when a locate rotating with continuity within the seat becomes inserted in a notch present in the base of the object.

3. The device as claimed in claim 2, wherein the rotating locator of the positioning station is made to rotate through an angle greater than 360°.

4. The device as claimed in claim 3, wherein the rotating locator of the positioning station is made to rotate through an angle of 450°.

5. The device as claimed in claim 2, wherein the rotating locator of the inspecting station is made to undergo continuous rotations of close to 360° overall.

6. The device as claimed in claim 5, wherein the rotating locator of the inspection station is associated with an encountering member having four mutually perpendicular arms which interfere in succession with a proximity sensor arranged to control the activation of the video camera.

7. The device as claimed in claim 1, comprising a single motor which by way of a transmission rotates the rotating locators present within the seat of the positioning station and within the seat of the inspection station.

8. The device as claimed in claim 7, wherein the locator rotating within the seat of the pre-positioning station can be disengaged from the drive motor.

9. An automatic device for determining print quality on objects of circular, elliptical or polygonal cross section, associated with a stepwise conveying line for the objects comprising a first horizontal crosspiece fixed to the machine base and carrying a series of idle equidistant nosepieces, a second crosspiece parallel to the first and carrying a series of seats aligned with said nosepieces, means for moving said two crosspieces towards and away from each other at each step of the conveying line, and at least one video camera overlying at least one of said nosepieces, wherein two consecutive seats of said series are braked, said seats comprising a rotating locator in their interior, said rotating locators being connected to a single motor which rotates them at different speeds which decrease in the direction of advancement of the objects.

10. The device as claimed in claim 9, wherein the rotating locator in that seat positioned upstream in the direction of advancement of the objects is connected to its transmission via a disengageable clutch.

11. The device as claimed in claim 9, wherein the rotating locator in that seat positioned downstream in the direction of advancement of the objects is connected to an encountering device with four mutually perpendicular arms which interfere with a sensor which controls the activation of a video camera overlying the conveying line at said seat.

12. The device as claimed in claim 9, comprising a pair of spotlights, of which the axes in the vertical plane converge onto the image to be photographed.

13. The device as claimed in claim 1, wherein said video camera successively photographs an image portion at each 90° rotation of the object carrying the image.

* * * * *